(12) United States Patent
Hiraoka

(10) Patent No.: US 11,317,786 B2
(45) Date of Patent: May 3, 2022

(54) ENDOSCOPE

(71) Applicant: OLYMPUS CORPORATION, Tokyo (JP)

(72) Inventor: Jin Hiraoka, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 420 days.

(21) Appl. No.: 16/388,971

(22) Filed: Apr. 19, 2019

(65) Prior Publication Data

US 2019/0239726 A1    Aug. 8, 2019

Related U.S. Application Data

(63) Continuation of application No. PCT/JP2017/039201, filed on Oct. 30, 2017.

(30) Foreign Application Priority Data

Oct. 28, 2016    (JP) .............................. JP2016-212012

(51) Int. Cl.
| | |
|---|---|
| *A61B 1/018* | (2006.01) |
| *A61B 1/00* | (2006.01) |
| *A61B 1/005* | (2006.01) |
| *A61B 8/12* | (2006.01) |
| *A61B 1/01* | (2006.01) |

(Continued)

(52) U.S. Cl.
CPC ............ *A61B 1/00098* (2013.01); *A61B 1/00* (2013.01); *A61B 1/0052* (2013.01); *A61B 1/01* (2013.01);

(Continued)

(58) Field of Classification Search
CPC ............................ A61B 1/00098; A61B 1/018
See application file for complete search history.

(56) References Cited

U.S. PATENT DOCUMENTS 5,868,663 A * 2/1999 Katsurada .............. A61B 1/018
                                                                               600/107
7,087,010 B2    8/2006   Ootawara et al.

(Continued)

FOREIGN PATENT DOCUMENTS

| JP | H05-103757 A | 4/1993 |
|---|---|---|
| JP | H08-243076 A | 9/1996 |

(Continued)

OTHER PUBLICATIONS

International Search Report dated Jan. 30, 2018 issued in PCT/JP2017/039201.

(Continued)

*Primary Examiner* — Matthew J Kasztejna
(74) *Attorney, Agent, or Firm* — Scully, Scott, Murphy & Presser, P.C.

(57) ABSTRACT

An endoscope includes an insertion unit configured to be inserted into a subject, and allow a treatment tool to protrude from a distal end thereof. The insertion unit includes: a rigid member having a treatment tool insertion hole; a raising base that adjusts, by turning, a protruding direction of the treatment tool; a first guide groove that is formed on an outer surface of the raising base and holds the treatment tool; and a second guide groove that is formed on at least a part of an inner surface of the treatment tool insertion hole and includes an opening having a width smaller than a diameter of the treatment tool insertion hole. The first guide groove and the second guide groove have the treatment tool interposed therebetween in all of set states of the raising base.

16 Claims, 18 Drawing Sheets

(51) Int. Cl.
*G02B 23/24* (2006.01)
*A61B 1/06* (2006.01)
*A61B 1/07* (2006.01)
*A61B 1/015* (2006.01)
*A61B 1/05* (2006.01)

(52) U.S. Cl.
CPC ............... *A61B 1/018* (2013.01); *A61B 8/12* (2013.01); *G02B 23/24* (2013.01); *A61B 1/00082* (2013.01); *A61B 1/00091* (2013.01); *A61B 1/00096* (2013.01); *A61B 1/00101* (2013.01); *A61B 1/00133* (2013.01); *A61B 1/015* (2013.01); *A61B 1/05* (2013.01); *A61B 1/0669* (2013.01); *A61B 1/07* (2013.01)

(56) References Cited

U.S. PATENT DOCUMENTS

2002/0091303 A1* 7/2002 Ootawara ................ A61B 1/01
600/106

2005/0228289 A1* 10/2005 Kohno ..................... A61B 8/14
600/463

FOREIGN PATENT DOCUMENTS

| | | |
|---|---|---|
| JP | H10-118072 A | 5/1998 |
| JP | H11-004804 A | 1/1999 |
| JP | H11-104062 A | 4/1999 |
| JP | 2002-034905 A | 2/2002 |
| JP | 2003-038426 A | 2/2003 |
| JP | 2004-267596 A | 9/2004 |
| JP | 2006-020725 A | 1/2006 |
| JP | 2008-017859 A | 1/2008 |
| WO | WO 2015/107801 A1 | 7/2015 |

OTHER PUBLICATIONS

Japanese Office Action dated Jun. 9, 2020 in Japanese Patent Application No. 2018-547836.

* cited by examiner

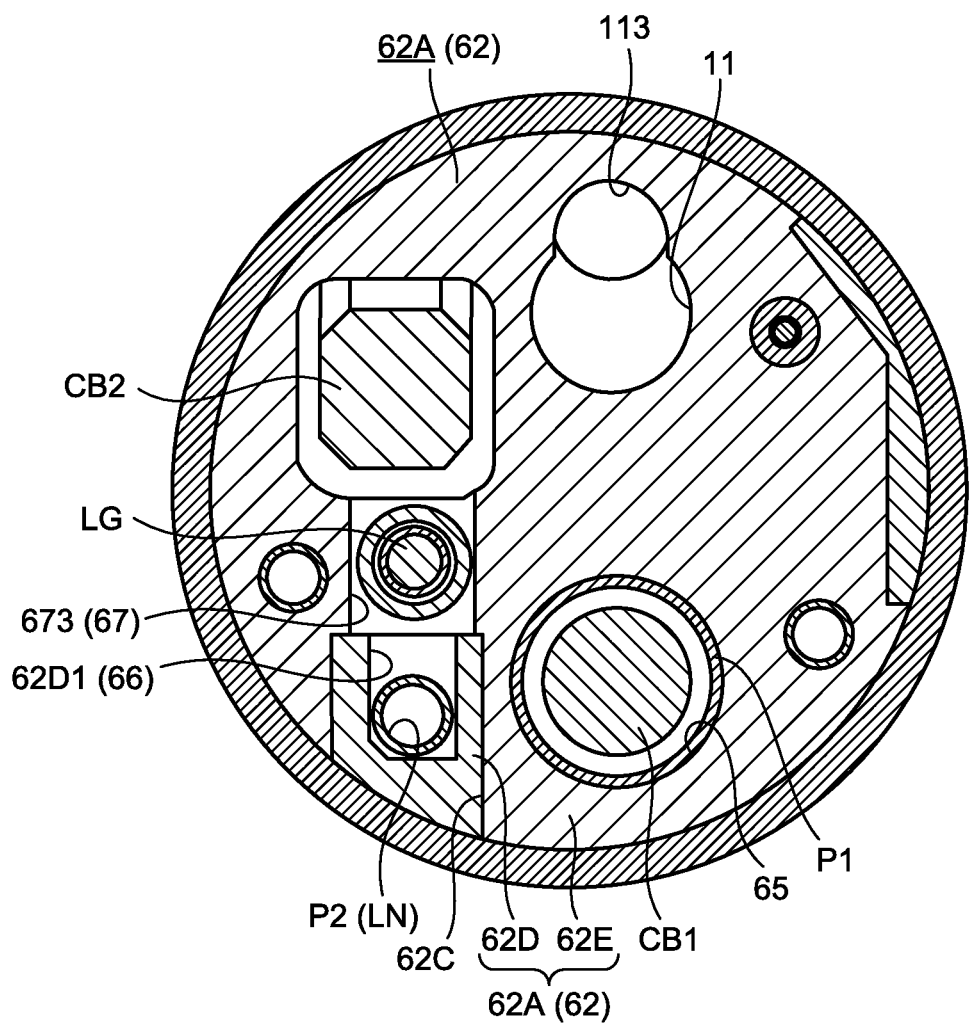

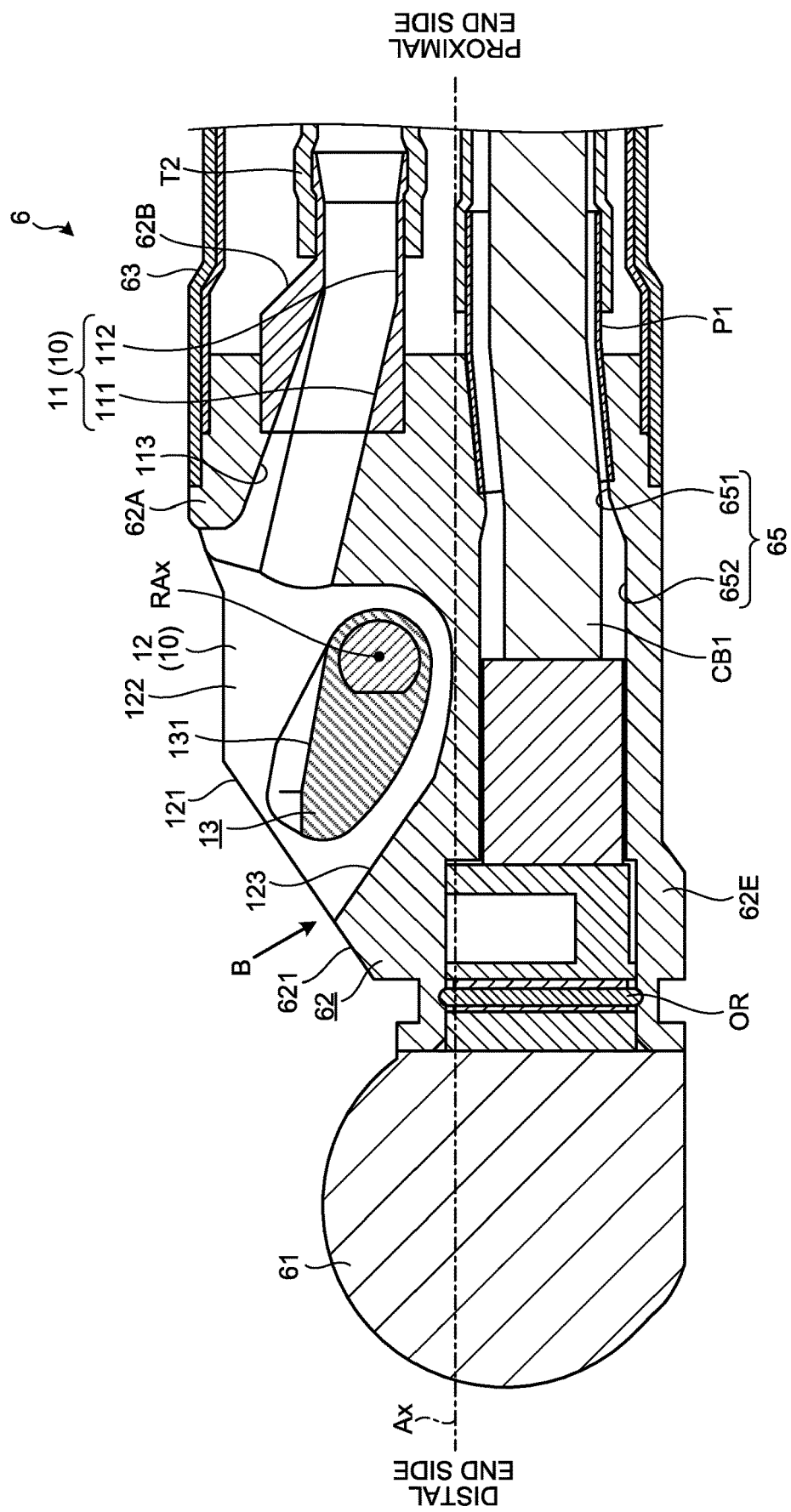

ENDOSCOPE

CROSS-REFERENCE TO RELATED APPLICATION

This application is a continuation of PCT International Application No. PCT/JP2017/039201 filed on Oct. 30, 2017, which designates the United States, incorporated herein by reference, and which claims the benefit of priority from Japanese Patent Application No. 2016-212012, filed on Oct. 28, 2016, incorporated herein by reference.

BACKGROUND

The present disclosure relates to an endoscope.

Endoscopes, which are for observation of the interior of a subject, such as a human, by insertion of a flexible and elongated insertion unit into the subject, have been known (see, for example, Japanese Laid-open Patent Publication No. 2004-267596).

An endoscope described in Japanese Laid-open Patent Publication No. 2004-267596 has a distal end portion and a forceps raising base, which are provided at a distal end side of the insertion unit of the endoscope. A "distal end side" referred to hereinafter means a distal end side of an insertion unit. Furthermore, a "proximal end side" referred to hereinafter means a side separated from a distal end of an insertion unit.

The distal end portion has a treatment tool protrusion hole formed therein, for insertion of a treatment tool therethrough.

The forceps raising base: is turnably attached to the distal end portion, on the distal end side of the treatment tool protrusion hole; and adjusts the protruding direction of the treatment tool that has protruded to the distal end side via the treatment tool protrusion hole, by turning. Furthermore, a wide engagement groove that is wide and a narrow engagement groove that is narrow are formed on the outer surface of the forceps raising base, correspondingly to various types of treatment tools having different sectional diameters. A treatment tool having a small sectional diameter is supported by the forceps raising base in a state where the outer peripheral surface of the treatment tool is in contact with the narrow engagement groove. Furthermore, a treatment tool having a large sectional diameter is supported by the forceps raising base in a state where the outer peripheral surface of the treatment tool is in contact with the wide engagement groove.

SUMMARY

An endoscope according to one aspect of the present disclosure includes an insertion unit configured to be inserted into a subject, and allow a treatment tool to protrude from a distal end thereof, the insertion unit including: a rigid member having a treatment tool insertion hole where the treatment tool is inserted; a raising base that is turnably attached to the rigid member on a distal end side of the treatment tool insertion hole, and adjusts, by turning, a protruding direction of the treatment tool that protrudes to the distal end side via the treatment tool insertion hole; a first guide groove that is formed on an outer surface of the raising base and holds the treatment tool; and a second guide groove that is formed on at least a part of an inner surface of the treatment tool insertion hole and includes an opening having a width smaller than a diameter of the treatment tool insertion hole, wherein the first guide groove and the second guide groove have the treatment tool interposed therebetween in all of set states of the raising base.

The above and other features, advantages and technical and industrial significance of this disclosure will be better understood by reading the following detailed description of presently preferred embodiments of the disclosure, when considered in connection with the accompanying drawings.

BRIEF DESCRIPTION OF THE DRAWINGS

FIG. 8B is a diagram illustrating a cross section of the rigid member, the cross section having been cut along a ninth plane;

FIG. 10A is a sectional view corresponding to FIG. 3, the sectional view being a diagram illustrating a temporary fixing structure for the light guide;

DETAILED DESCRIPTION

Described hereinafter by reference to the drawings is a mode (hereinafter, the embodiment) for carrying out the present disclosure. The present disclosure is not limited to the embodiment described below. Furthermore, throughout the drawings, each part is assigned with the same reference sign.

Schematic Configuration of Endoscope System

Figure 1:
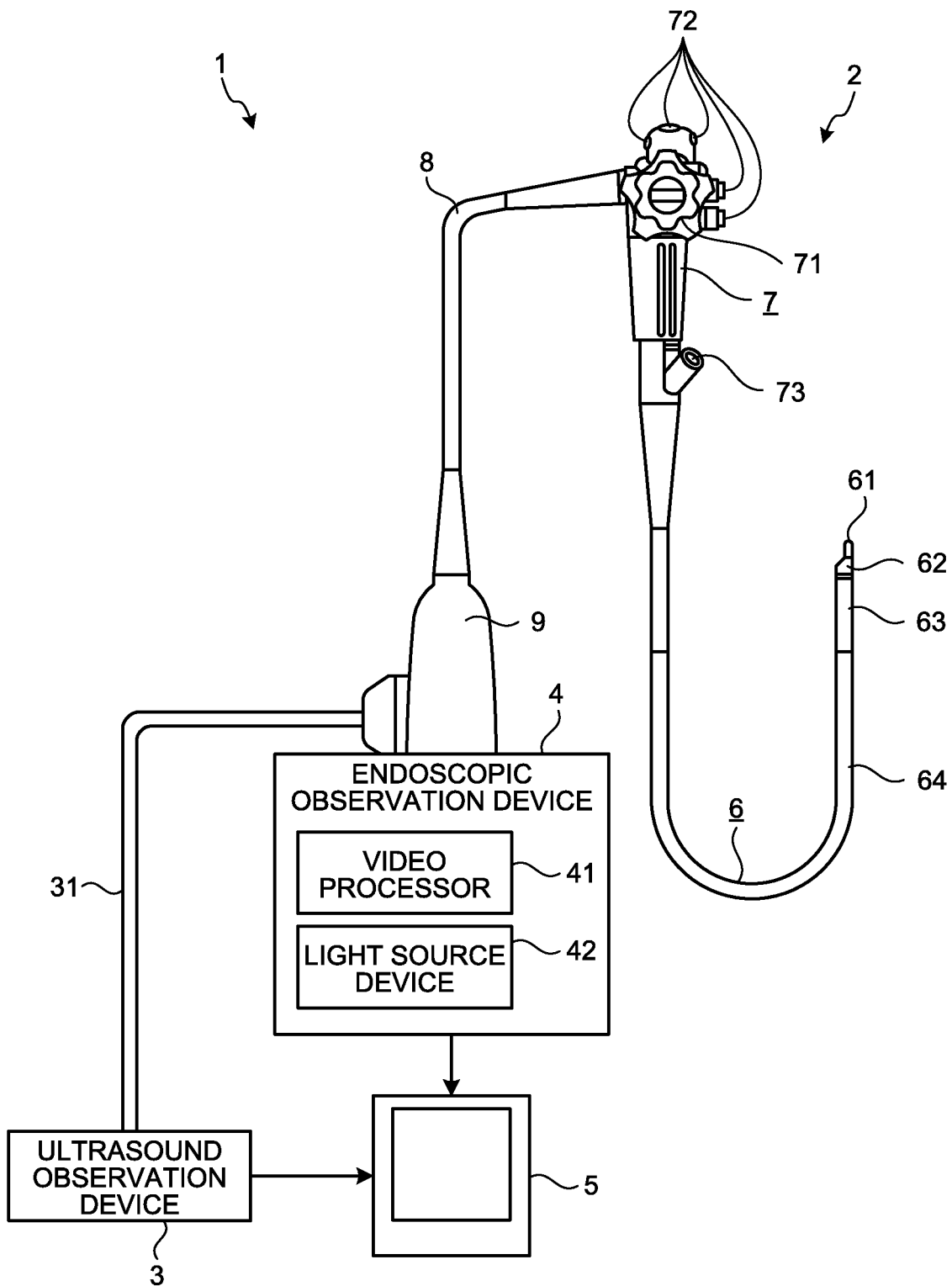
FIG. 1 is a diagram schematically illustrating an endoscope system according to an embodiment.

FIG. 1 is a diagram schematically illustrating an endoscope system 1 according to an embodiment.

The endoscope system 1 is a system for ultrasound diagnosis of the interior of a subject, such as a human, by use of an ultrasound endoscope. This endoscope system 1 includes, as illustrated in FIG. 1, an ultrasound endoscope 2, an ultrasound observation device 3, an endoscopic observation device 4, and a display device 5.

The ultrasound endoscope 2 has functions of an endoscope. This ultrasound endoscope 2 has a part that is able to be inserted into a subject, and has: a function of transmitting ultrasound pulses toward a body wall inside the subject, receiving an ultrasound echo reflected in the subject, and outputting an echo signal; and a function of capturing an image of the interior of the subject and outputting an image signal.

A detailed configuration of the ultrasound endoscope 2 will be described later.

The ultrasound observation device 3 is electrically connected to the ultrasound endoscope 2 via an ultrasound cable 31 (see FIG. 1); and outputs a pulse signal to the ultrasound endoscope 2 and receives an echo signal from the ultrasound endoscope 2, via the ultrasound cable 31. The ultrasound observation device 3 generates an ultrasound image by performing predetermined processing on the echo signal.

A later described endoscope connector 9 (FIG. 1) of the ultrasound endoscope 2 is freely attachably and detachably connected to the endoscopic observation device 4. The endoscopic observation device 4 includes, as illustrated in FIG. 1, a video processor 41, and a light source device 42.

The video processor 41 receives an image signal from the ultrasound endoscope 2 via the endoscope connector 9. The video processor 41 generates an endoscopic image by performing predetermined processing on the image signal.

The light source device 42 supplies illumination light for illuminating the interior of a subject, to the ultrasound endoscope 2 via the endoscope connector 9.

The display device 5 is formed by use of liquid crystal or organic electroluminescence (EL), and displays thereon an ultrasound image generated by the ultrasound observation device 3, an endoscopic image generated by the endoscopic observation device 4, and the like.

Configuration of Ultrasound Endoscope

Described next is a configuration of the ultrasound endoscope 2.

The ultrasound endoscope 2 includes, as illustrated in FIG. 1, an insertion unit 6, an operating unit 7, a universal cord 8, and the endoscope connector 9.

Figure 2:
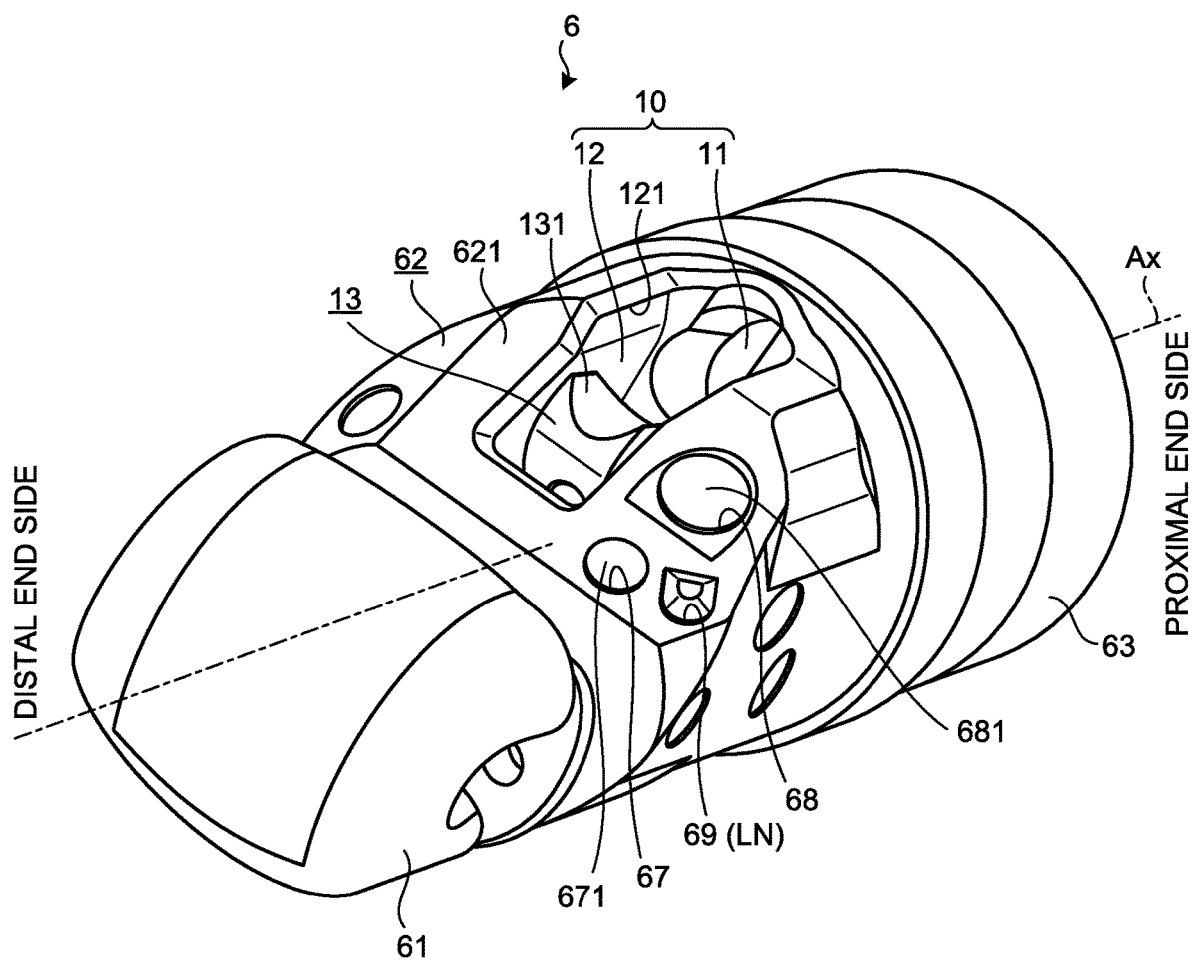
FIG. 2 is a perspective view illustrating a distal end of an insertion unit.

FIG. 2 is a perspective view illustrating a distal end of the insertion unit 6.

A "distal end side" referred to hereinafter means a distal end side of the insertion unit 6 (a distal end side in the direction of insertion into a subject). Furthermore, a "proximal end side" referred to hereinafter means the side separated from the distal end of the insertion unit 6.

The insertion unit 6 is a part to be inserted into a subject. This insertion unit 6 includes, as illustrated in FIG. 1 or FIG. 2: an ultrasound probe 61 provided at the distal end side; a rigid member 62 connected to a proximal end of the ultrasound probe 61; a bending portion 63 that is connected to a proximal end of the rigid member 62 and is bendable; and a flexible tube 64 that is connected to a proximal end of the bending portion 63 and has flexibility.

The insertion unit 6, the operating unit 7, the universal cord 8, and the endoscope connector 9 have: laid therein, a light guide LG (see FIG. 8A) that transmits therethrough the illumination light supplied from the light source device 42, a transducer cable CB1 (see FIG. 10A) that transmits therethrough the above described pulse signal and echo signal, and a signal cable CB2 (see FIG. 8A) that transmits therethrough an image signal; and provided therein, a conduit line LN (see FIG. 2 and FIG. 8A) for fluid to flow therethrough.

Described hereinafter are configurations of the ultrasound probe 61 and the rigid member 62 from among the members 61 to 64 forming the insertion unit 6.

The ultrasound probe 61 is a convex ultrasound probe, and has plural ultrasound transducers (illustration thereof being omitted in the drawings) regularly arranged to form a convex circular arc. The ultrasound probe 61 adopted is not necessarily a convex ultrasound probe, and may be a radial ultrasound probe.

Each of the ultrasound transducers includes an acoustic lens, a piezoelectric element, and a matching layer, and acquires an ultrasound echo contributing to an ultrasound tomographic image of a part inside a subject, the part being more inward than the subject's body wall.

The ultrasound probe 61 converts a pulse signal received from the ultrasound observation device 3 via the ultrasound cable 31 and the transducer cable CB1, into ultrasound pulses, and transmits the ultrasound pulses into the subject. Furthermore, the ultrasound probe 61 converts an ultrasound echo reflected inside the subject, into an electric echo signal, and outputs the electric echo signal via the transducer cable CB1 and the ultrasound cable 31, to the ultrasound observation device 3.

The rigid member 62 has a substantially cylindrical shape extending along an insertion axis Ax (see FIG. 2). The insertion axis Ax is an axis along the extending direction of the insertion unit 6.

This rigid member 62 has an inclined surface 621 formed on its outer peripheral surface at the distal end side, the inclined surface 621 making the rigid member 62 tapered toward a distal end of the rigid member 62.

The rigid member 62 has an attachment hole 65 (see FIG. 10A) and a balloon hole 66 (see FIG. 8A) each penetrating therethrough from the proximal end to the distal end of the rigid member 62. Furthermore, the rigid member 62 has, formed therein, as illustrated in FIG. 2, an illumination hole 67, an imaging hole 68, an air and water feeding hole 69, a treatment tool channel 10, and the like, each of which penetrates therethrough from the proximal end of the rigid member 62 to the inclined surface 621.

The attachment hole 65 is a hole where the ultrasound probe 61 is to be attached. The attachment hole 65 has the transducer cable CB1 inserted therethrough, the transducer cable CB1 being electrically connected to the ultrasound probe 61 (see FIG. 10A). According to this embodiment, the attachment hole 65 is formed of: a first attachment hole 651 (see FIG. 10A) that is inclined to an outer peripheral side of the rigid member 62 from a proximal end to a distal end thereof and extends linearly; and a second attachment hole 652 (see FIG. 10A) that communicates with the first attachment hole 651 and extends linearly from the first attachment hole 651 along the insertion axis Ax to the distal end of the rigid member 62. Furthermore, the first and second attachment holes 651 and 652 are connected to each other without a bump on the inner surface of the attachment hole 65 (a bump that would catch the transducer cable CB1 when the transducer cable CB1 is inserted through the attachment hole 65). The first attachment hole 651 has a connection pipe P1 (see FIG. 10A) fitted therein, the connection pipe P1 being inclined at the distal end side correspondingly to the inclination of the first attachment hole 651 and extending along the insertion axis Ax at the proximal end side. That is, the transducer cable CB1 is inserted through the attachment hole 65 via the connection pipe P1.

The balloon hole 66 is a hole that forms a part of the conduit line LN and is: for water to be filled into a balloon (illustration thereof being omitted in the drawings), which has been attached to the distal end of the insertion unit 6 so that the balloon covers the ultrasound probe 61; or for the water in the balloon to be sucked out. The balloon hole 66 has one end of the balloon pipe P2 (see FIG. 8A) fitted therein. Furthermore, the other end of the balloon pipe P2 has a balloon tube T1 (see FIG. 8A) attached thereto, the balloon tube T1 having been laid inside the insertion unit 6, the operating unit 7, the universal cord 8, and the endoscope connector 9. Similarly to the balloon hole 66, these balloon pipe P2 and balloon tube T1 each form a part of the conduit line LN. That is, water is filled into a balloon or water in the balloon is sucked out, via the balloon hole 66, the balloon pipe P2, and the balloon tube T1.

The illumination hole 67 has, arranged therein, an emission end of the light guide LG, and an illumination lens 671 (see FIG. 2), through which illumination light emitted from the emission end of the light guide LG is emitted into a subject. According to this embodiment, the illumination hole 67 is formed of: a first illumination hole 672 (see FIG. 8A) that extends linearly along a substantially normal direction of the inclined surface 621 from the inclined surface 621; and a second illumination hole 673 (see FIG. 8A) that communicates with the first illumination hole 672 and linearly extends along the insertion axis Ax, from the first illumination hole 672 to the proximal end of the rigid member 62. The illumination lens 671 is arranged in the first illumination hole 672. Furthermore, the emission end of the light guide LG is arranged in the illumination hole 67 in a state of being bent correspondingly to the inclination of the first illumination hole 672.

An attachment structure for the light guide LG and the balloon pipe P2 will be described later.

The imaging hole 68 has, arranged therein: an objective optical system 681 (FIG. 2) that condenses light (a subject image) that has been emitted into the subject and reflected in the subject; and an imaging element (illustration thereof being omitted in the drawings) that captures the subject image condensed by the objective optical system 681. An image signal captured by the imaging element is transmitted to the endoscopic observation device 4 (the video processor 41) via the signal cable CB2.

As described above, according to the embodiment, the illumination hole 67 and the imaging hole 68 are formed on the inclined surface 621. Therefore, the ultrasound endoscope 2 according to the embodiment is formed as an oblique viewing type endoscope for observation in a direction intersecting the insertion axis Ax at an acute angle.

The air and water feeding hole 69 is a hole that forms a part of the conduit line LN, and is for feeding air or feeding water to the imaging hole 68 and washing the outer surface of the objective optical system 681.

The treatment tool channel 10 is a channel, through which a treatment tool Tt (see FIG. 5A), such as a puncture needle, that has been inserted through the insertion unit 6, protrudes to the outside. This treatment tool channel 10 includes, as illustrated in FIG. 2, a treatment tool insertion hole 11 and a housing groove 12.

The treatment tool insertion hole 11 extends from the proximal end of the rigid member 62 to the distal end side, and communicates with a treatment tool tube T2 (see FIG. 3) that has been laid inside the flexible tube 64 and bending portion 63 from a later described treatment tool insertion opening 73 in the operating unit 7. The treatment tool insertion hole 11 has the treatment tool Tt inserted therethrough via the treatment tool tube T2.

According to this embodiment, a part of the rigid member 62 is formed of a connection member 62B (see FIG. 3) made of metal, the part being where the treatment tool tube T2 is connected, and the other part of the rigid member 62 is formed of a resin member 62A (see FIG. 3) made of resin. The treatment tool insertion hole 11 is formed over both the resin member 62A and the connection member 62B. This resin member 62A corresponds to a rigid member body according to the present disclosure.

The housing groove 12 is a groove that communicates with the treatment tool insertion hole 11 and extends from the treatment tool insertion hole 11, along the insertion axis Ax, to the distal end side.

The housing groove 12 has a raising base 13 housed therein, which is housed turnably around a rotation axis RAx (see FIG. 3) and which adjusts the protruding direction of the treatment tool Tt from the housing groove 12 by coming into contact with the treatment tool Tt that has been inserted through the housing groove 12 via the treatment tool insertion hole 11.

Detailed shapes of the treatment tool channel 10 and the raising base 13 will be described later.

The operating unit 7 is a portion that is connected to a proximal end of the insertion unit 6 and receives various operations from a medical doctor or the like. This operating unit 7 includes, as illustrated in FIG. 1, a bending knob 71 for bending operation on the bending portion 63, and plural operating members 72 for performing various operations.

Furthermore, the operating unit 7 has the treatment tool insertion opening 73 provided therein, which communicates with the treatment tool insertion hole 11 via the treatment tool tube T2, and which is for inserting the treatment tool Tt through the treatment tool tube T2.

The universal cord 8 extends from the operating unit 7, and has, arranged therein, the light guide LG, the transducer cable CB1, the signal cable CB2, a tube (illustration thereof being omitted in the drawings) forming a part of the conduit line LN, and the like.

The endoscope connector 9 is provided at an end portion of the universal cord 8. The endoscope connector 9 has the ultrasound cable 31 connected thereto, and is connected to the video processor 41 and the light source device 42 by being plugged into the endoscopic observation device 4.

Shapes of Treatment Tool Channel and Raising Base

Described next are shapes of the treatment tool channel 10 and the raising base 13.

Figure 3:
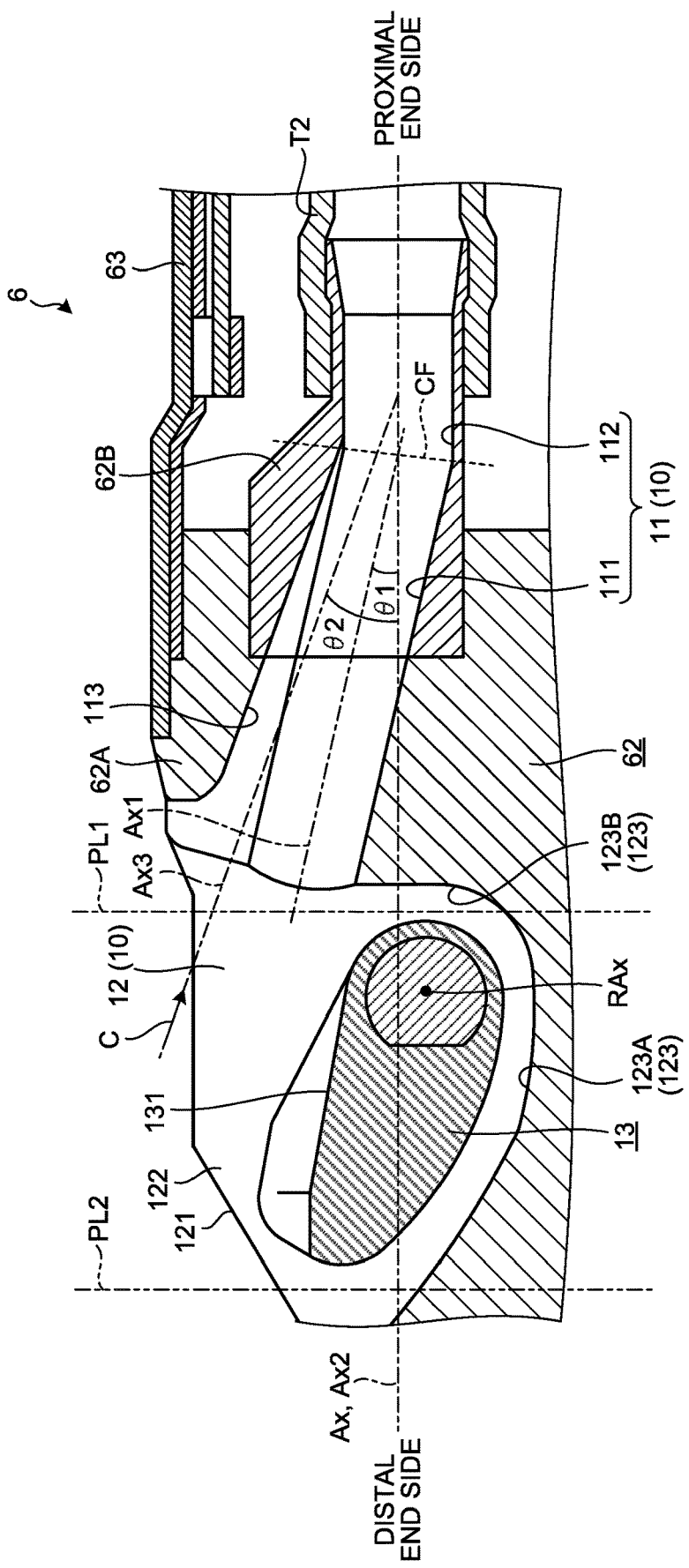
FIG. 3 is a diagram illustrating shapes of a treatment tool channel and a raising base.
Figure 4A:
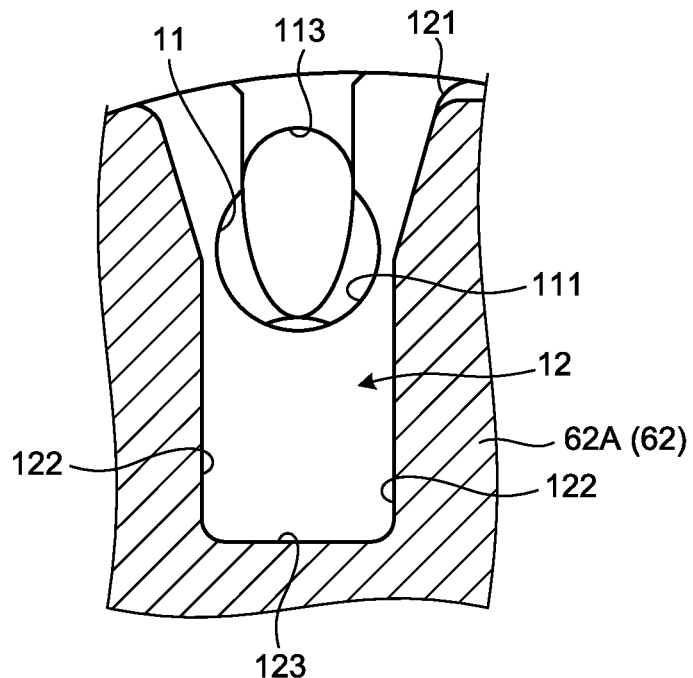
FIG. 4A is a diagram illustrating a cross section of a rigid member, the cross section having been cut along a first plane.
Figure 4B:
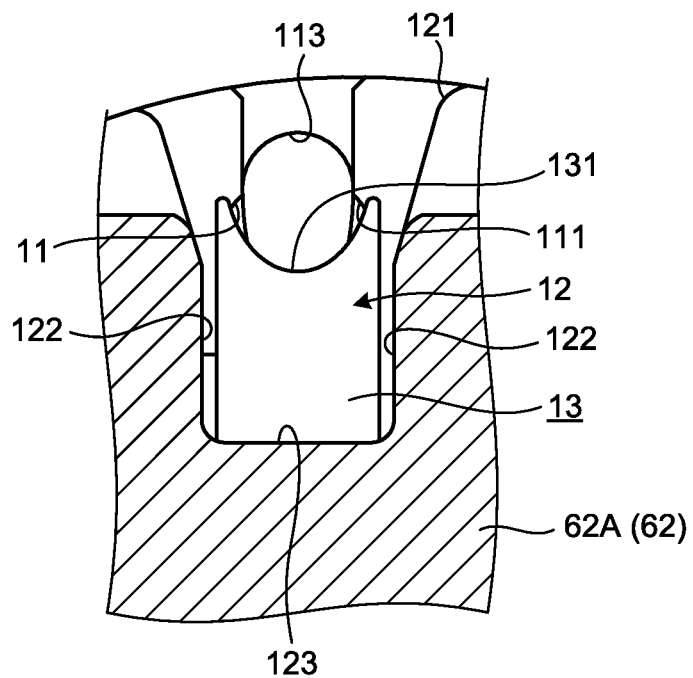
FIG. 4B is a diagram illustrating a cross section of the rigid member, the cross section having been cut along a second plane.
Figure 4C:
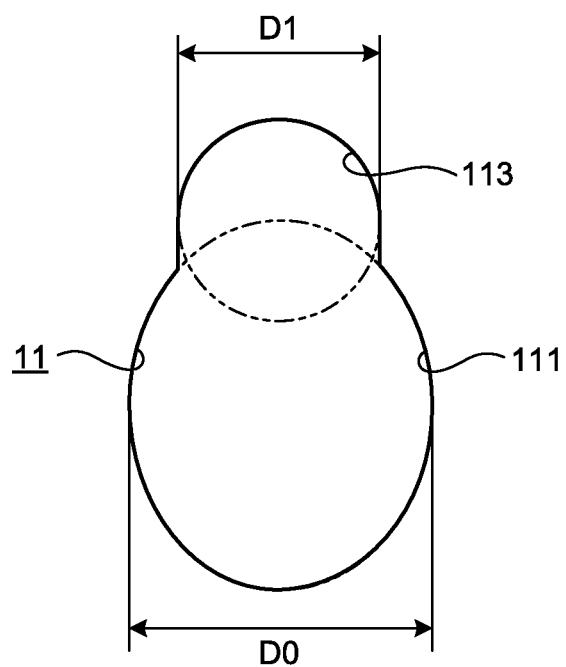
FIG. 4C is a diagram illustrating a treatment tool insertion hole as viewed in a direction represented by an arrow C illustrated in FIG. 3.

FIG. 3 is a diagram illustrating the shapes of the treatment tool channel 10 and the raising base 13. FIG. 4A and FIG. 4B are diagrams illustrating cross sections of the rigid member 62 respectively cut along a first plane PL1 and a second plane PL2. FIG. 4C is a diagram illustrating the treatment tool insertion hole 11 as viewed in a direction represented by an arrow C illustrated in FIG. 3.

Specifically, FIG. 3 is a sectional view of the rigid member 62 cut along a cutting plane, which is along the insertion axis Ax and which passes the housing groove 12. Furthermore, the first plane PL1 illustrated in FIG. 3 is a plane orthogonal to the insertion axis Ax and positioned between the treatment tool insertion hole 11 and the raising base 13. Moreover, the second plane PL2 illustrated in FIG. 3 is a plane orthogonal to the insertion axis Ax and positioned on the distal end side of the raising base 13. FIG. 3, FIG. 4A, and FIG. 4B illustrate a state where the raising base 13 has been set in a lowered state. In addition, in FIG. 4A and FIG. 4B, cross sections respectively cut along the first plane PL1 and second plane PL2 are being viewed from the distal end side.

Hereinafter, upper in FIG. 3 (closer to an opening 121 of the housing groove 12) will be referred to as "upper", and lower in FIG. 3 will be referred to as "lower".

The treatment tool insertion hole 11 is formed of, as illustrated in FIG. 3, an inclined insertion hole 111 and a proximal end insertion hole 112.

The inclined insertion hole 111 is a hole having a circular cross section in, is inclined at a first angle θ1 (FIG. 3) with respect to the insertion axis Ax, and extends linearly from a distal end of the treatment tool insertion hole 11 to the proximal end side. The reference sign, "Ax1", illustrated in FIG. 3 represents the central axis of the inclined insertion hole 111.

The proximal end insertion hole 112: is a hole having the same diameter as the inclined insertion hole 111 and having a circular cross section; communicates with the inclined insertion hole 111; and extends linearly along the insertion axis Ax from the inclined insertion hole 111 to a proximal end of the treatment tool insertion hole 11. The reference sign, "Ax2", illustrated in FIG. 3 represents the central axis of the proximal end insertion hole 112.

Hereinafter, for convenience of explanation, the interface between the inclined insertion hole 111 and the proximal end insertion hole 112 will be referred to as a bending plane CF (FIG. 3).

As illustrated in FIG. 3 and FIG. 4A to FIG. 4C, a second guide groove 113 is formed on the inner surface of the treatment tool insertion hole 11.

The second guide groove 113 is formed at an upper side of the inner surface of the treatment tool insertion hole 11 (at a side opposite to a later described first guide groove 131 in the raising base 13), and extends up to a part of the inner surface of the proximal end insertion hole 112 over the bending plane CF from a distal end of the inner surface of the inclined insertion hole 111. More specifically, the second guide groove 113 has an arc-shaped cross section having a diameter dimension smaller than that of the inclined insertion hole 111 or the proximal end insertion hole 112, the arc-shaped cross section being slightly larger than a sectional diameter of the treatment tool Tt. Furthermore, a width D1 of an opening of the second guide groove 113 (FIG. 4C) is smaller than a diameter D0 of the inclined insertion hole 111 or the proximal end insertion hole 112 (FIG. 4C). Moreover, the second guide groove 113 extends linearly to be inclined at a second angle θ2 (FIG. 3) larger than the first angle θ1, with respect to the insertion axis Ax. The reference sign, "Ax3", illustrated in FIG. 3 represents the central axis of the second guide groove 113.

Functions of the second guide groove 113 will be described later.

In the housing groove 12, a pair of side wall surfaces 122 are respectively formed of flat surfaces, which are each orthogonal to the rotation axis RAx and parallel to each other. Furthermore, as illustrated in FIG. 4A or FIG. 4B, upper portions of the pair of side wall surfaces 122 are formed to be separated from each other upward and to gradually increase the width dimension of the housing groove 12.

Moreover, in the housing groove 12, a bottom portion 123 has a shape described below. Hereinafter, the bottom portion 123 has a distal end side bottom portion 123A (FIG. 3) at the distal end side with reference to the first plane PL1, and a proximal end side bottom portion 123B (FIG. 3) at the proximal end side with reference to the first plane PL1.

As illustrated in FIG. 3, the distal end side bottom portion 123A is formed of a curved surface that is curved upward toward a distal end thereof from a boundary position between the distal end side bottom portion 123A and the proximal end side bottom portion 123B, this distal end forming a rim portion of the opening 121.

As illustrated in FIG. 3, the proximal end side bottom portion 123B is formed of a surface that extends upward from the boundary position between the distal end side bottom portion 123A and the proximal end side bottom portion 123B, the surface having an upper end forming the rim portion of the opening 121 and being substantially planar. The treatment tool insertion hole 11 (the inclined insertion hole 111 and the second guide groove 113) penetrates the proximal end side bottom portion 123B and communicates with the housing groove 12.

The raising base 13 is formed of a columnar body having a cross section that is substantially elliptical (FIG. 3) and extending along the rotation axis RAx. In this raising base 13, the first guide groove 131 extending along the circumferential direction of the outer peripheral surface of the raising base is formed on the outer peripheral surface, as illustrated in FIG. 3 or FIG. 4B, the outer peripheral surface facing upward. This first guide groove 131 has a cross section, which is slightly larger than the diameter dimension of the treatment tool Tt and which is substantially arc-shaped.

Functions of the first guide groove 131 will be described later.

One end of the raising base 13 is pivotally supported in the housing groove 12 such that the raising base 13 is turnable around the rotation axis RAx, the one end being at an end side of the major axis of the substantially elliptical cross section. The raising base 13 is turned by transmission of the motive power via a wire or the like, the motive power corresponding to a user operation on the operating unit 7 by a medical doctor or the like, and is set in a raised state where the raising base 13 has been raised relatively to the insertion axis Ax (see FIG. 6A and FIG. 7A) or the lowered state where the raising base 13 has been lowered from the raised state (FIG. 3).

Functions of First and Second Guide Grooves

Described next are functions of the first and second guide grooves 131 and 113.

Figure 5A:
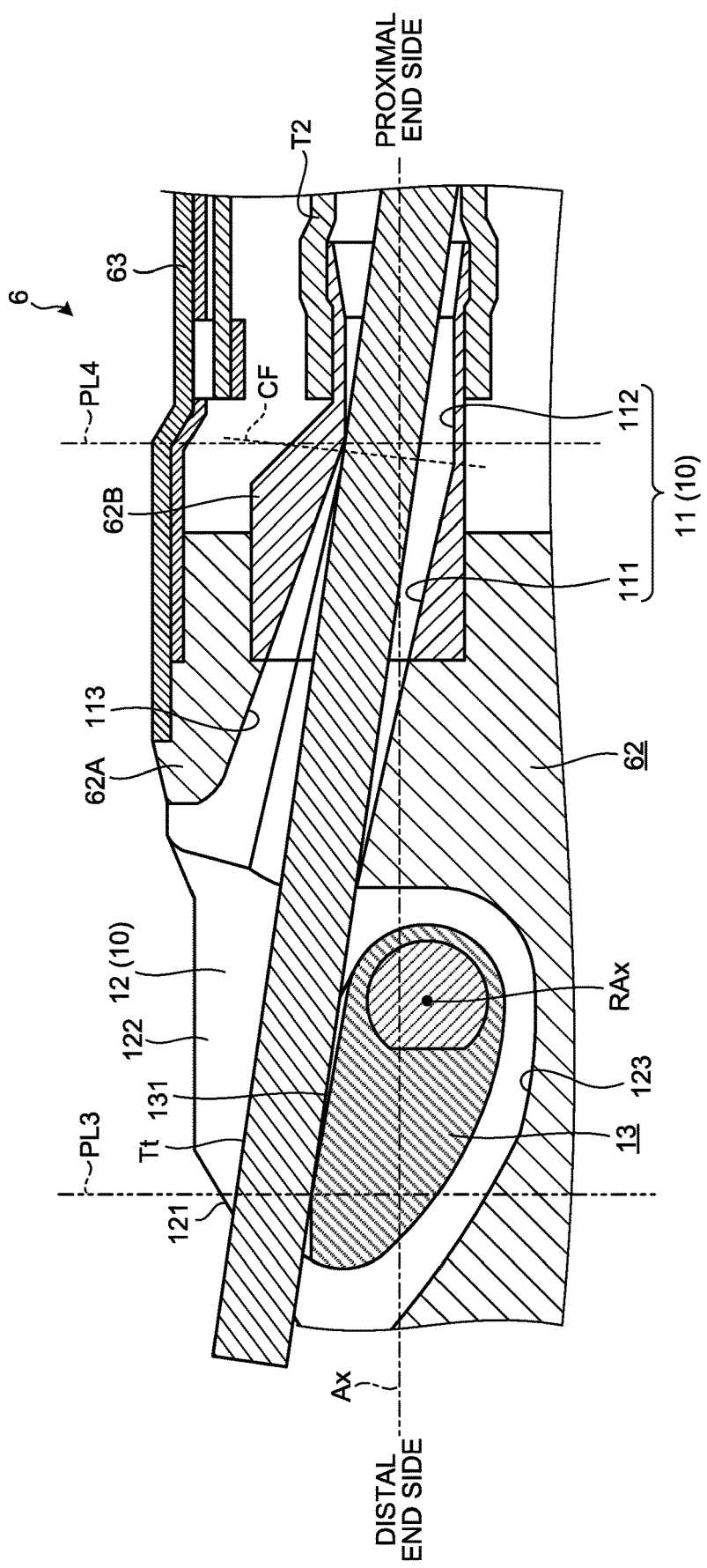
FIG. 5A is a sectional view corresponding to FIG. 3, the sectional view being a diagram illustrating the orientation of a treatment tool when the raising base has been set in a lowered state.
Figure 5B:
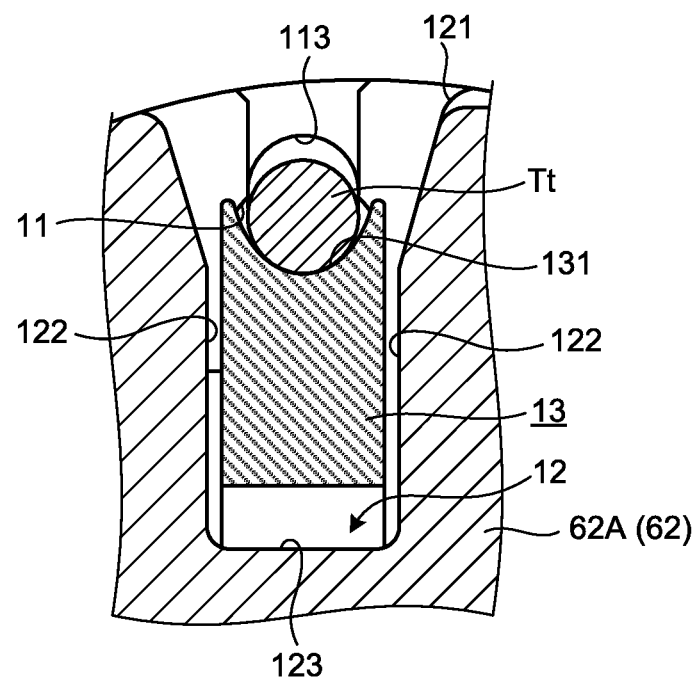
FIG. 5B is a diagram illustrating a cross section that has been cut along a third plane in the state illustrated in FIG. 5A.
Figure 5C:
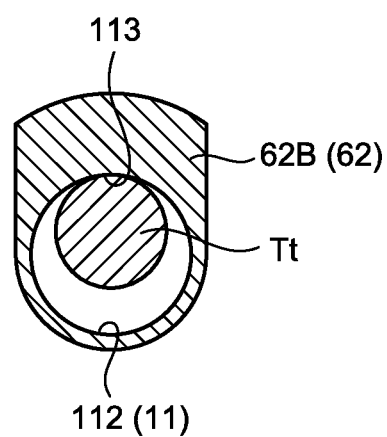
FIG. 5C is a diagram illustrating a cross section that has been cut along a fourth plane in the state illustrated in FIG. 5A.
Figure 6A:
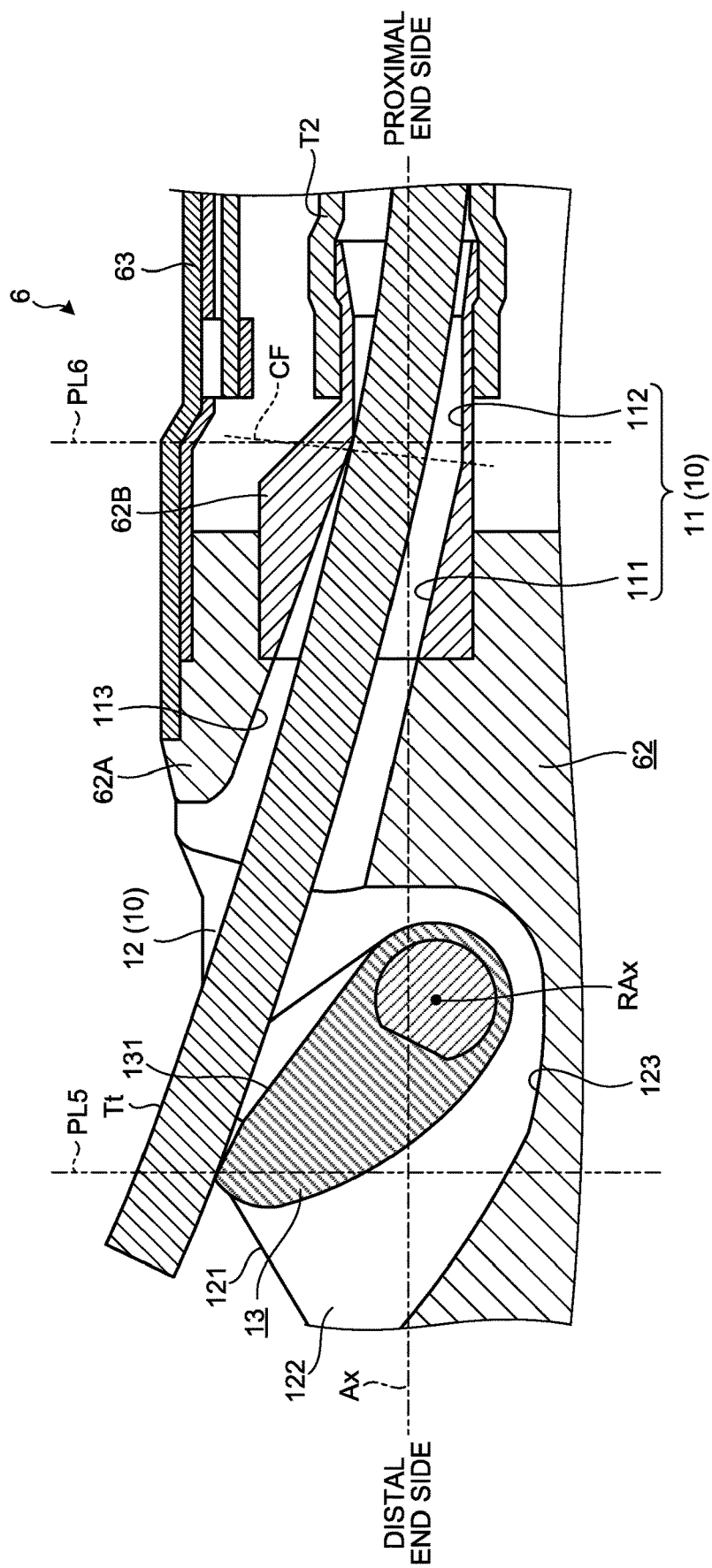
FIG. 6A is a sectional view corresponding to FIG. 3, the sectional view being a diagram illustrating the orientation of the treatment tool when the raising base has been raised from the lowered state.
Figure 6B:
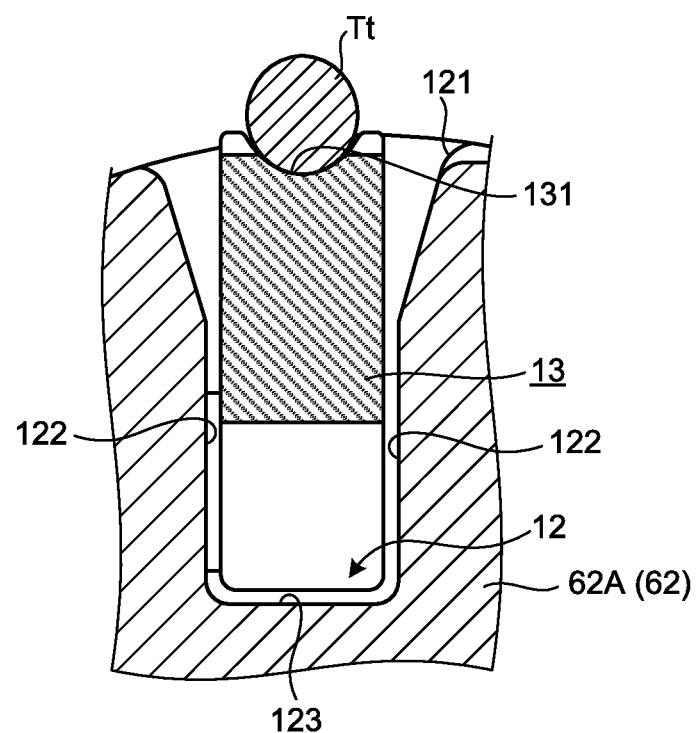
FIG. 6B is a diagram illustrating a cross section that has been cut along a fifth plane in the state illustrated in FIG. 6A.
Figure 6C:
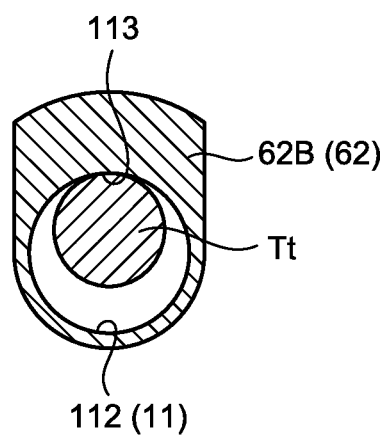
FIG. 6C is a diagram illustrating a cross section cut along a sixth plane in the state illustrated in FIG. 6A.
Figure 7A:
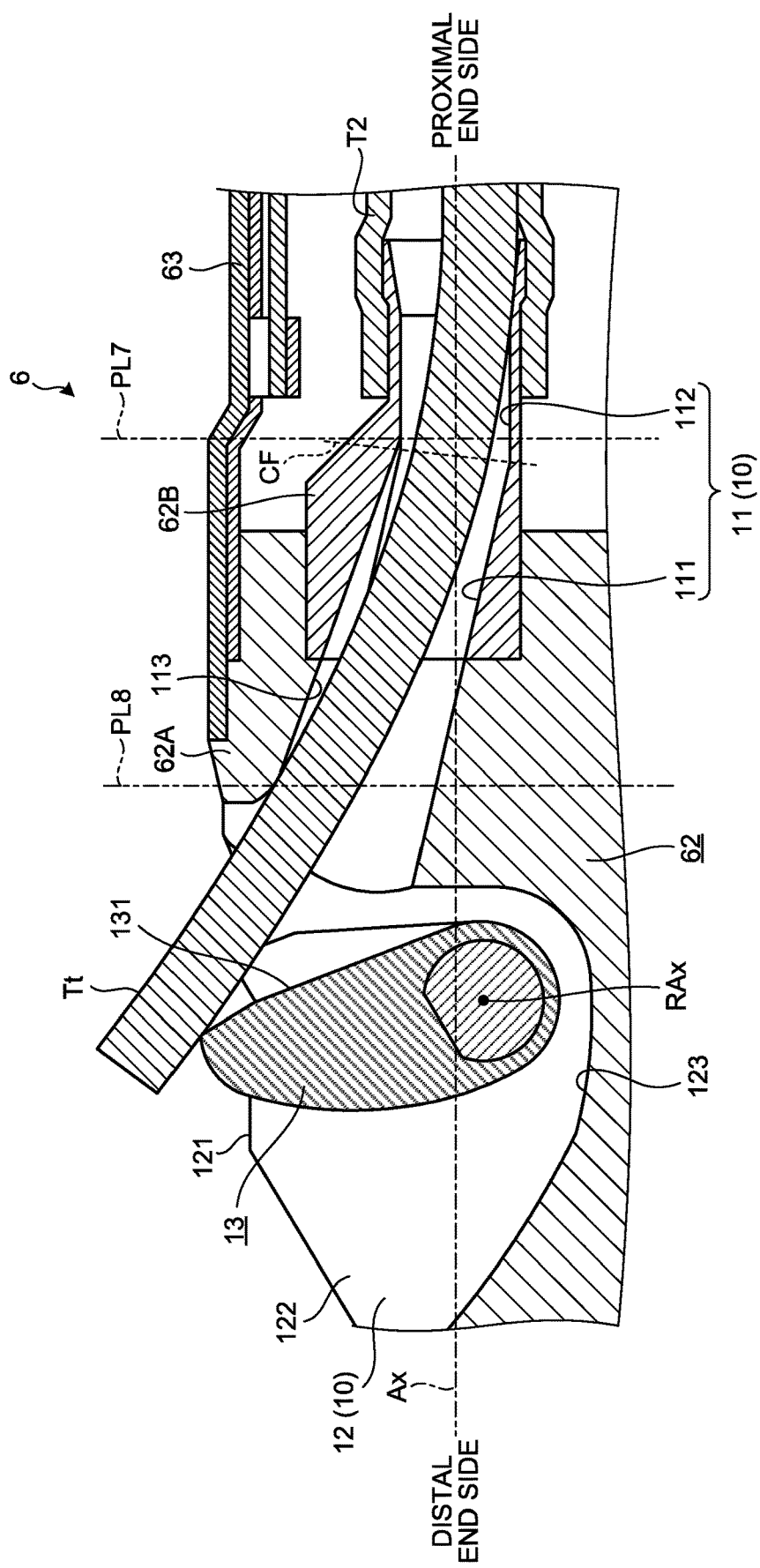
FIG. 7A is a sectional view corresponding to FIG. 3, the sectional view being a diagram illustrating the orientation of the treatment tool when the raising base has been set in a maximally raised state.
Figure 7B:
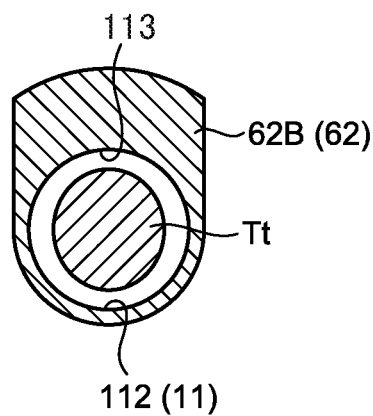
FIG. 7B is a diagram illustrating a cross section cut along a seventh plane in the state illustrated in FIG. 7A.
Figure 7C:
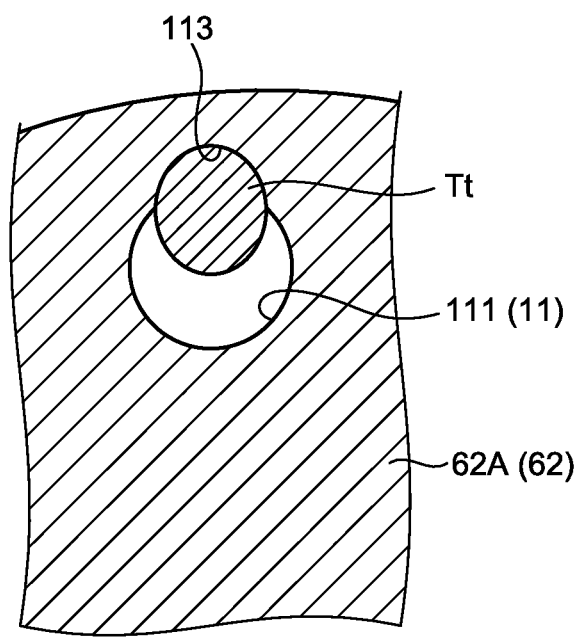
FIG. 7C is a diagram illustrating a cross section cut along an eighth plane in the state illustrated in FIG. 7A.

FIG. 5A is a diagram illustrating the orientation of the treatment tool Tt when the raising base 13 has been set in the lowered state. FIG. 5B and FIG. 5C are diagrams illustrating cross sections respectively cut along third and fourth planes PL3 and PL4 in the state illustrated in FIG. 5A. FIG. 6A is a diagram illustrating the orientation of the treatment tool Tt when the raising base 13 has been raised from the lowered state. FIG. 6B and FIG. 6C are diagrams illustrating cross sections respectively cut along fifth and sixth planes PL5 and PL6 in the state illustrated in FIG. 6A. FIG. 7A is a diagram illustrating the orientation of the treatment tool Tt when the raising base 13 has been set in a maximally raised state. FIG. 7B and FIG. 7C are diagrams illustrating cross sections respectively cut along seventh and eighth planes PL7 and PL8 in the state illustrated in FIG. 7A.

Specifically, FIG. 5A, FIG. 6A, and FIG. 7A are sectional views corresponding to FIG. 3. Furthermore, the third and fifth planes PL3 and PL5 respectively illustrated in FIG. 5A and FIG. 6A are planes orthogonal to the insertion axis Ax and passing through a contact position between the treatment tool Tt and the raising base 13. Moreover, the fourth, sixth, and seventh planes PL4, PL6, and PL7 respectively illustrated in FIG. 5A, FIG. 6A, and FIG. 7A are planes orthogonal to the insertion axis Ax and positioned near the bending plane CF. In addition, the eighth plane PL8 illustrated in FIG. 7A is a plane orthogonal to the insertion axis Ax and positioned at the distal end side of the treatment tool insertion hole 11. In FIG. 5B, FIG. 5C, FIG. 6B, FIG. 6C, FIG. 7B, and FIG. 7C, the cross sections respectively cut along the third to eight planes PL3 to PL8 are being viewed from the distal end side.

Described at first is the orientation of the treatment tool Tt protruding from the distal end side of the insertion unit 6 via the treatment tool channel 10 when the raising base 13 has been set in the lowered state.

A portion of the treatment tool Tt is oriented to extend substantially linearly, as illustrated in FIG. 5A, the portion being positioned in the treatment tool channel 10. A distal end of the outer peripheral surface of that portion of the treatment tool Tt comes into contact with the first guide groove 131 (FIG. 5B) and a proximal end of the outer peripheral surface of that portion of the treatment tool Tt comes into contact with a portion of the second guide groove 113, the portion being near the bending plane CF (FIG. 5C). That is, the treatment tool Tt is brought into a state of being interposed between the first and second guide grooves 131 and 113.

Described next is the orientation of the treatment tool Tt when the raising base 13 has been raised from the lowered state.

Since a distal end of the treatment tool Tt is raised upward by the raising base 13, as illustrated in FIG. 6A, the treatment tool Tt is oriented to be curved upward toward the distal end from a fulcrum that is a position where the treatment tool Tt has come into contact with the second guide groove 113 (near the bending plane CF). In this state also, as illustrated in FIG. 6B and FIG. 6C, the treatment tool Tt is in a state of being interposed between the first and second guide grooves 131 and 113.

Lastly described is the orientation of the treatment tool Tt when the raising base 13 has been set in the maximally raised state.

When the treatment tool Tt is raised further from the state illustrated in FIG. 6A, the position where the upward curve starts is shifted to the proximal end side gradually from the position near the bending plane CF. As a result, the outer peripheral surface of the treatment tool Tt separates from the portion of the second guide groove 113 (FIG. 7B), the portion being near the bending plane CF, and comes into contact with a portion of the second guide groove 113, the portion being at the distal end side (FIG. 7C). That is, in this state also, the treatment tool Tt is in the state of being interposed between the first and second guide grooves 131 and 113.

As described above, the first and second guide grooves 131 and 113 have the function of having the treatment tool Tt interposed therebetween in all of these set states of the raising base 13.

Attachment Structure for Light Guide and Balloon Pipe

Described next is an attachment structure for the light guide LG and the balloon pipe P2.

Figure 8A:
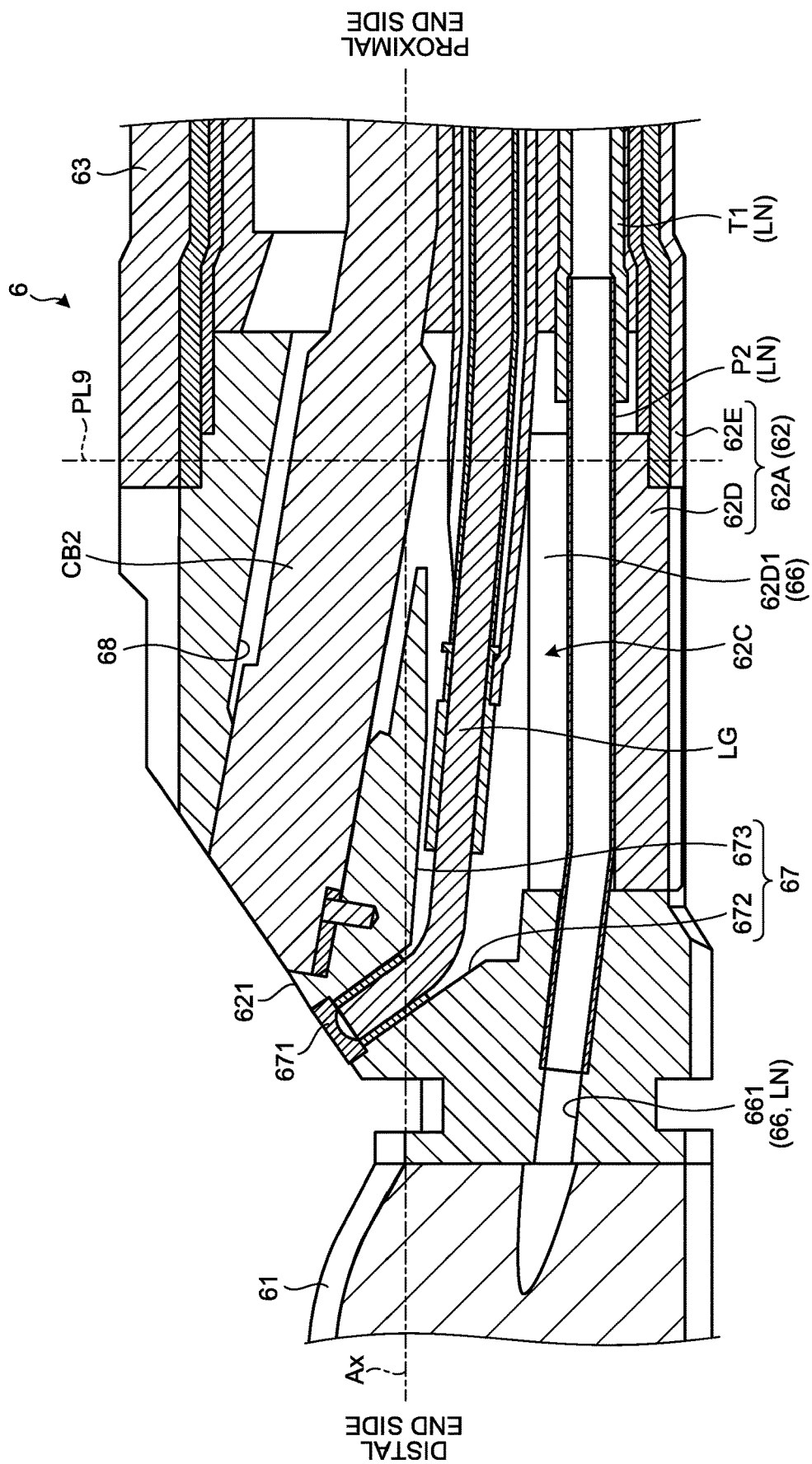
FIG. 8A is a diagram illustrating an attachment structure for a light guide and a balloon pipe.

FIG. 8A is a diagram illustrating the attachment structure for the light guide LG and the balloon pipe P2. FIG. 8B is a diagram illustrating a cross section of the rigid member 62, the cross section having been cut along a ninth plane PL9.

Specifically, FIG. 8A is a sectional view of the rigid member 62 cut along a cutting plane along the insertion axis Ax and passing through the holes 66 to 68. Furthermore, the ninth plane PL9 illustrated in FIG. 8A is a plane orthogonal to the insertion axis Ax and positioned at the distal end side of the resin member 62A. In FIG. 8B, the cross section cut along the ninth plane PL9 is being viewed from the proximal end side.

The outer peripheral surface of the resin member 62A has, as illustrated in FIG. 8A or FIG. 8B: a recessed groove 62C formed therein, which extends to the distal end side from a proximal end thereof; and a lid 62D attached thereto, which closes the recessed groove 62C.

Hereinafter, for convenience of explanation, a portion of the resin member 62A, the portion being other than the lid 62D, will be referred to as a resin member body 62E (FIG. 8A and FIG. 8B). That is, the resin member 62A is formed of the resin member body 62E and the lid 62D.

As illustrated in FIG. 8A or FIG. 8B, the recessed groove 62C has a depth dimension, so as to go through the balloon hole 66 from the outer peripheral surface of the resin member body 62E and to communicate with the second illumination hole 673.

The lid 62D has an outer surface having a shape that is substantially the same as the shape of the inner surface of the recessed groove 62C, and closes the recessed groove 62C by being fitted in the recessed groove 62C. This lid 62D has, as illustrated in FIG. 8A or FIG. 8B, a U-shaped groove 62D1 formed therein, which extends from a proximal end to a distal end of the lid 62D. In a state where the lid 62D has been fitted in the recessed groove 62C, the U-shaped groove 62D1 forms a part of the balloon hole 66.

Hereinafter, for convenience of explanation, a portion of the balloon hole 66 will be referred to as a first balloon hole 661 (see FIG. 8A), the portion being formed in the resin member body 62E.

Described hereinafter is the procedure of attachment of the light guide LG and the balloon pipe P2.

Figure 9:
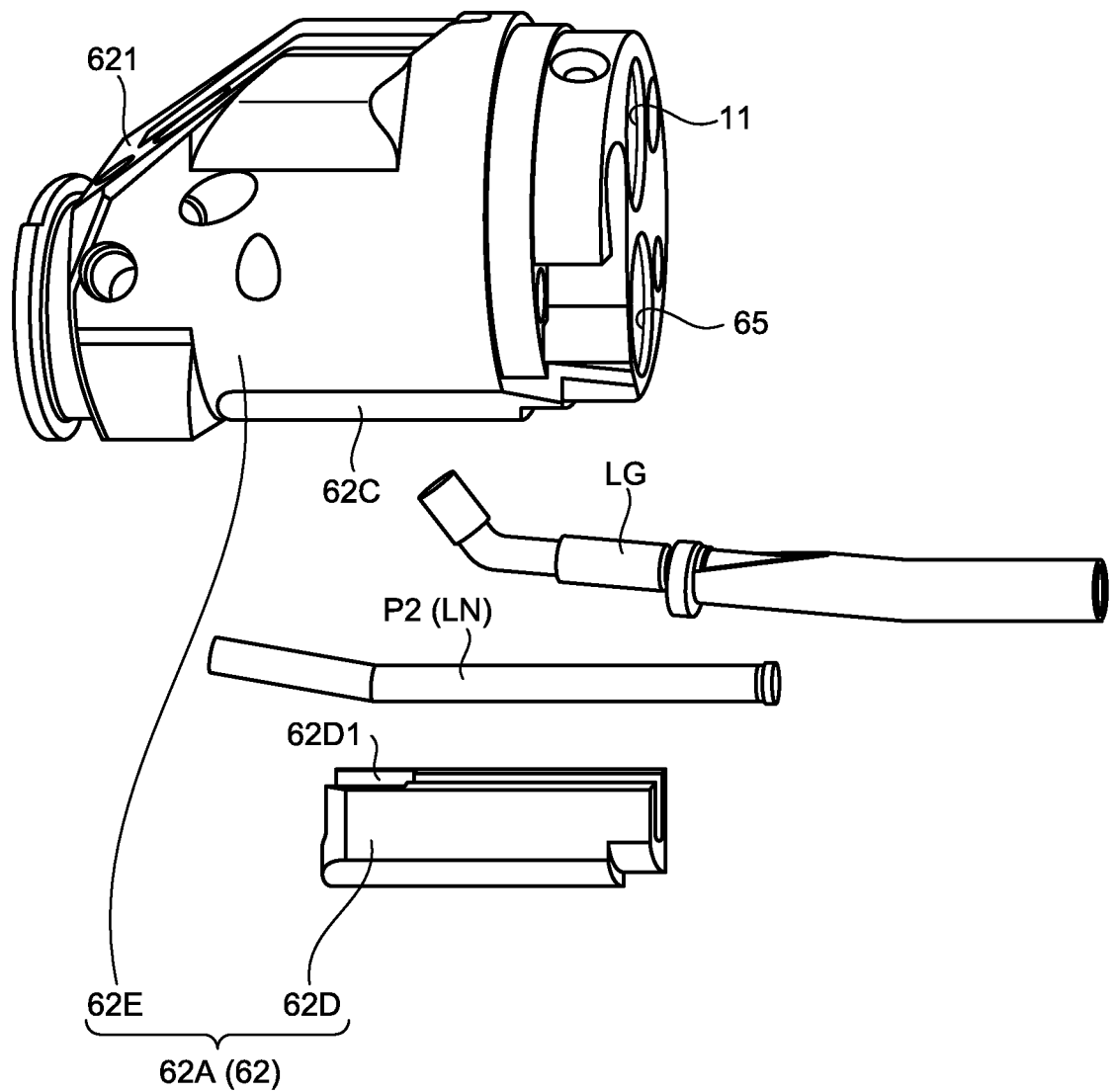
FIG. 9 is a diagram for explanation of the procedure of attachment of the light guide and the balloon pipe.

FIG. 9 is a diagram illustrating the procedure of attachment of the light guide LG and the balloon pipe P2.

Specifically, FIG. 9 is an exploded perspective view having therein the resin member body 62E, the lid 62D, the light guide LG, and the balloon pipe P2 separated from each other.

Firstly, an operator inserts the emission end of the light guide LG into the first illumination hole 672 via the recessed groove 62C. Thereafter, the operator performs positioning of the emission end of the light guide LG with respect to the illumination lens 671, and temporarily fixes the emission end of the light guide LG to the resin member body 62E. After this temporary fixing, the operator injects an adhesive into the illumination hole 67, and permanently fixes the emission end of the light guide LG to the resin member body 62E.

A temporary fixing structure for the light guide LG will be described later.

Subsequently, the operator inserts one end of the balloon pipe P2 into the first balloon hole 661. Thereafter, the operator fits (fixes) the lid 62D into the recessed groove 62C such that the balloon pipe P2 is inserted through the U-shaped groove 62D1. The operator then connects the balloon tube T1 to the other end of the balloon pipe P2.

Temporary Fixing Structure for Light Guide

Described next is the temporary fixing structure for the light guide LG.

Figure 10B:
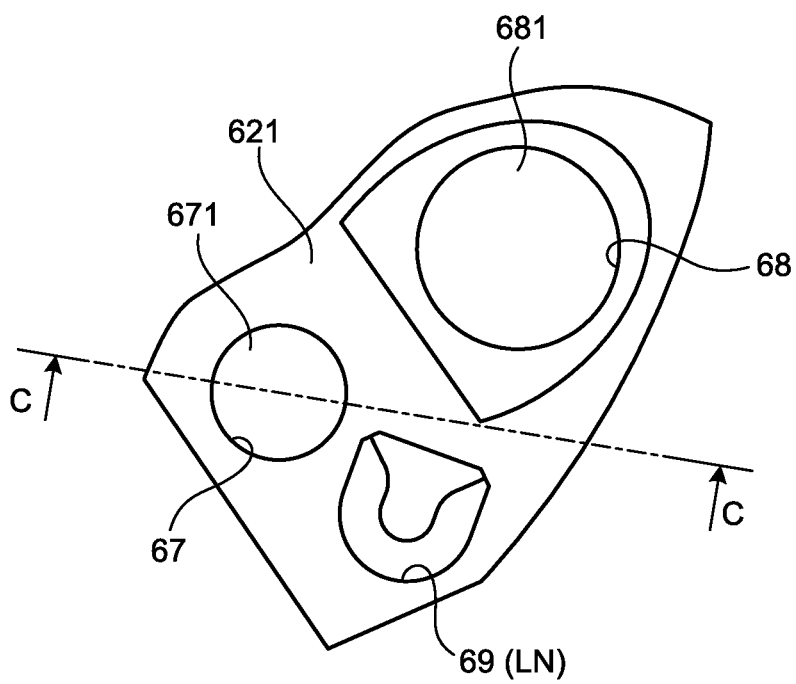
FIG. 10B is a diagram illustrating an inclined surface as viewed in a direction represented by an arrow B illustrated in FIG. 10A.
Figure 10C:
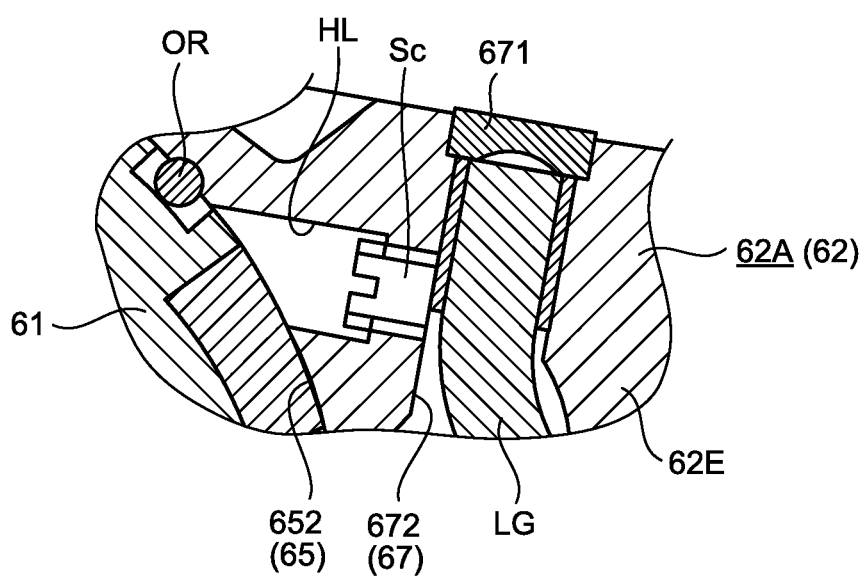
FIG. 10C is a sectional view along a C-C line illustrated in FIG. 10B.
Figure 11:
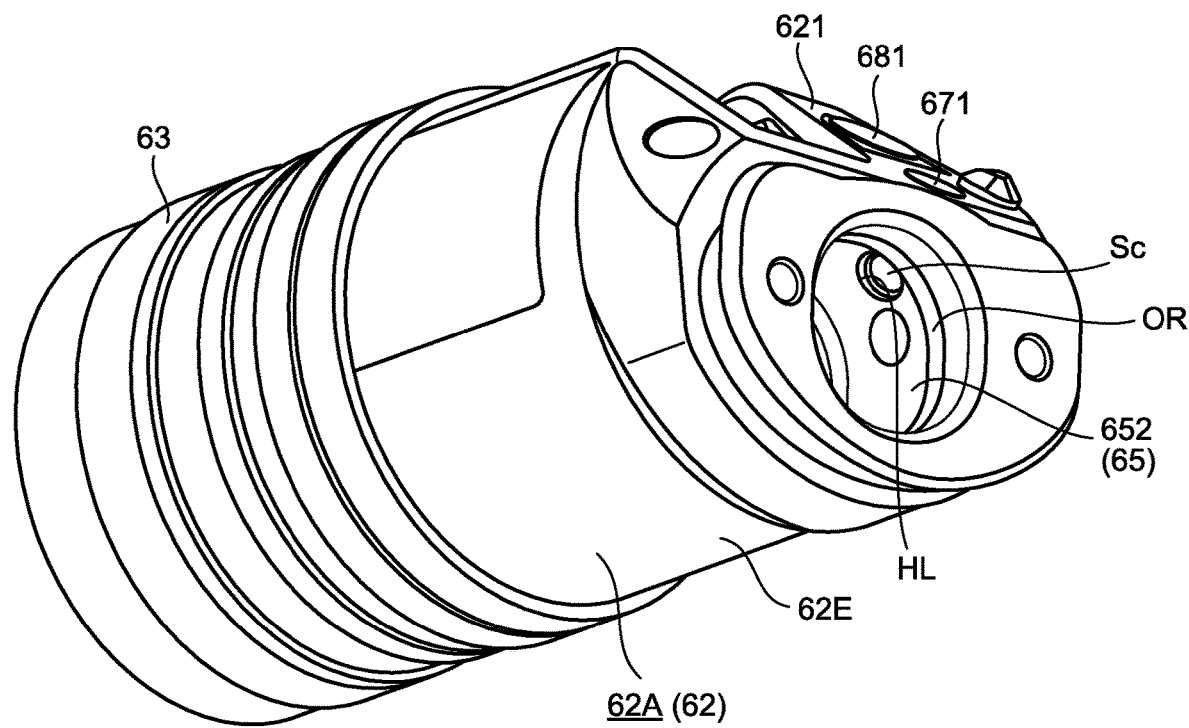
FIG. 11 is a perspective view of the rigid member as viewed from a distal end side, in a state where an ultrasound probe has been removed therefrom.

FIG. 10A is a sectional view corresponding to FIG. 3, the sectional view being a diagram illustrating the temporary fixing structure for the light guide LG. FIG. 10B is a diagram illustrating the inclined surface 621 as viewed in a direction represented by an arrow B illustrated in FIG. 10A. FIG. 10C is a sectional view along a C-C line illustrated in FIG. 10B. FIG. 11 is a perspective view of the rigid member 62 as viewed from the distal end side, in a state where the ultrasound probe 61 has been removed therefrom.

A screw Sc (FIG. 10C and FIG. 11) is used in the temporary fixing of the light guide LG.

Specifically, the resin member body 62E has a screw hole HL (FIG. 10C and FIG. 11) formed therein, which penetrates therethrough between the first illumination hole 672 and the second attachment hole 652 and which has a screw groove on a part of the inner surface of the screw hole HL. This screw hole HL communicates with the second attachment hole 652 on the proximal end side of the position where an O-ring OR (FIG. 10C and FIG. 11) is arranged. This O-ring OR is a member that is attached to the outer surface of the ultrasound probe 61 and prevents liquid from entering the first attachment hole 651 from between the outer surface of the ultrasound probe 61 and the inner surface of the second attachment hole 652. In FIG. 11, for convenience of explanation, in illustration of the position where the O-ring OR is arranged, the O-ring OR is positioned on the inner surface of the second attachment hole 652.

When the operator temporarily fixes the light guide LG, the operator inserts the screw Sc into the screw hole HL through the second attachment hole 652, and causes one end of the screw Sc to protrude toward the first illumination hole 672 by screwing the screw Sc into the screw groove of the screw hole HL. That is, the emission end of the light guide LG, the emission end being positioned in the first illumination hole 672, is temporarily fixed by the screw Sc that has protruded into the first illumination hole 672.

The above described ultrasound endoscope 2 according to the embodiment has the following effects.

In the ultrasound endoscope 2 according to the embodiment, the first guide groove 131 is formed on the outer surface of the raising base 13. Furthermore, the treatment tool insertion hole 11 has the second guide groove 113 formed therein. Distal and proximal end parts of the treatment tool Tt, the distal and proximal end parts being separated from each other, respectively come into contact with the first and second guide grooves 131 and 113, and are interposed between the first and second guide grooves 131 and 113.

Therefore, the ultrasound endoscope 2 according to the embodiment has an effect of enabling reduction of wobbling of the treatment tool Tt that has protruded from the distal end of the insertion unit 6.

In particular, adopted according to the embodiment is the configuration where the distal and proximal end parts of the treatment tool Tt are respectively supported by the first and second guide grooves 131 and 113, the distal and proximal end parts being separate from each other. Accordingly, by two points of the treatment tool Tt being supported, the two points being separate from each other in the longitudinal direction of the treatment tool Tt, wobbling of the treatment tool Tt is able to be reduced more infallibly, as compared to a configuration where a single point that is a distal end portion of the treatment tool Tt is interposed therebetween.

If the diameter dimension of the treatment tool insertion hole 11 is set to be the same as the diameter dimension of the second guide groove 113 without formation of the second guide groove 113, any treatment tool Tt, such as a puncture needle, which has a sectional diameter smaller than the diameter dimension of the second guide groove 113, is able to be used. However, any treatment tool Tt having a sectional diameter larger than the diameter dimension of the second guide groove 113 is unable to be used.

In the ultrasound endoscope 2 according to the embodiment, the diameter D0 of the treatment tool insertion hole 11 is larger than the width D1 of the opening of the second guide groove 113. Therefore, not only treatment tools Tt, such as puncture needles, which have small sectional diameters, but also treatment tools Tt having large sectional diameters are able to be used.

Furthermore, in the ultrasound endoscope 2 according to the embodiment, the second guide groove 113 extends up to a part of the inner surface of the proximal end insertion hole 112 from the distal end of the inner surface of the inclined insertion hole 111 over the bending plane CF. Moreover, the second guide groove 113 extends linearly to be inclined at the second angle θ2 larger than the first angle θ1 with respect to the insertion axis Ax.

Therefore, the treatment tool Tt is interposed between the first and second guide grooves 131 and 113 in all of the set states of the raising base 13, and thus wobbling of the treatment tool Tt is able to be reduced (FIG. 5A to FIG. 5C, FIG. 6A to FIG. 6C, and FIG. 7A to FIG. 7C).

In a case where the rigid member body 62A and the connection member 62B are integrally formed of a resin material, upon molding of the resin material, a thin portion serving as a connection portion to the treatment tool tube T2 is unable to be formed thinly in terms of strength, and thus the diameter of the whole rigid member 62 will become large.

In the ultrasound endoscope 2 according to the embodiment, only the rigid member body 62A is formed of a resin material, and the connection member 62B is formed of a metallic material. That is, since the connection member 62B where the treatment tool tube T2 is connected is formed of a metallic material, even if a thin portion serving as the connection portion to the treatment tool tube T2 is formed comparatively thinly, the strength is able to maintained sufficiently. Therefore, as compared to the case where the rigid member body 62A and the connection member 62B are integrally formed of a resin material, the diameter of the whole rigid member 62 is able to be made small.

Even if the rigid member body 62A and the connection member 62B are integrally formed of a metallic material, the above effect of enabling reduction in the diameter of the whole rigid member 62 is achieved, and thus the rigid member body 62A and the connection member 62B may be integrally formed of a metallic material.

Furthermore, in the ultrasound endoscope 2 according to the embodiment, the insertion unit 6 includes the ultrasound probe 61 at the distal end of the rigid member 62. That is, since wobbling of the treatment tool Tt is able to be reduced as described above, the treatment tool Tt is able to be prevented from being displaced from a scanned surface of the ultrasound probe 61, and whether or not the treatment tool Tt has reached a target part is able to be checked easily.

Other Embodiments

The mode for carrying out the present disclosure has been described thus far, but the present disclosure is not to be limited only to the above described embodiment.

According to the above described embodiment, the endoscope system 1 has both the function of generating an ultrasound image and the function of generating an endoscopic image, but not being limited thereto, the endoscope system 1 may be configured to have only one of these functions.

The endoscope system 1 according to the above described embodiment may be an endoscope system for observation of the interior of a subject, such as a mechanical structure in the industrial field, without being limited to its use in the medical field.

The ultrasound endoscope 2 according to the above described embodiment is formed as an oblique viewing type endoscope for observation in a direction intersecting the insertion axis Ax at an acute angle, but not being limited thereto, the ultrasound endoscope 2 may be formed as a side viewing type endoscope for observation in a direction intersecting the insertion axis Ax at right angles.

Figure 12A:
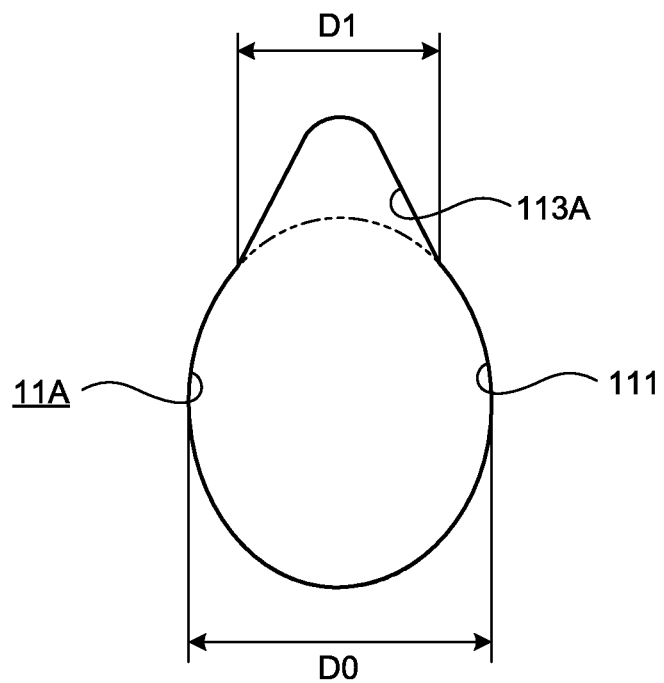
FIG. 12A is a diagram illustrating a treatment tool insertion hole according to a modified example of the embodiment.
Figure 12B:
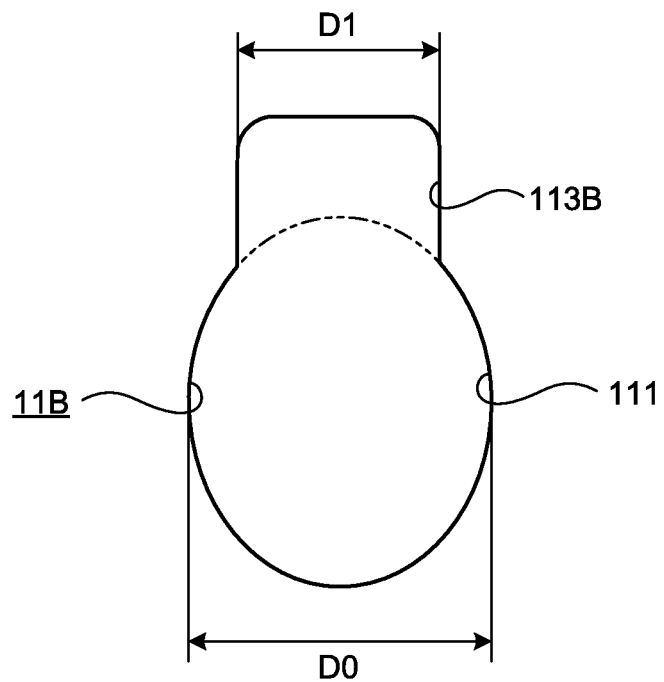
FIG. 12B is a diagram illustrating a treatment tool insertion hole according to another modified example of the embodiment.

FIG. 12A and FIG. 12B are diagrams illustrating treatment tool insertion holes 11A and 11B according to modified examples of the embodiment. Specifically, FIG. 12A and FIG. 12B are diagrams corresponding to FIG. 4C.

According to the above described embodiment, the second guide groove 113 has an arc-shaped cross section, but not being limited thereto, the second guide groove 113 may be formed to be shaped differently.

For example, as illustrated in FIG. 12A, a second guide groove 113A may have a cross section that is substantially V-shaped. Furthermore, as illustrated in FIG. 12B, a second guide groove 113B may have a cross section that is substantially rectangular. When the second guide grooves 113A and 113B are formed as illustrated therein, the widths D1 of openings of the second guide grooves 113A and 113B are also preferably set to be smaller than the diameter D0 of the inclined insertion hole 111.

According to the above described embodiment and the modified examples illustrated in FIG. 12A and FIG. 12B, the second guide grooves 113, 113A, and 113B are each formed in at least a part of the inner surface of the treatment tool insertion hole 11, 11A, or 11B. That is, like the above described embodiment and the modified examples illustrated in FIGS. 12A and 12B, the second guide grooves 113, 113A, and 113B may each be formed in only a part of the treatment tool insertion hole 11, 11A, or 11B; or the second guide grooves 113, 113A, and 113B may each be formed over the entire length of the treatment tool insertion hole 11, 11A, or 11B.

According to the above described embodiment and the modified examples illustrated in FIG. 12A and FIG. 12B, the second guide grooves 113, 113A, and 113B are each formed to extend inclinedly at the second angle $\theta 2$ larger than the first angle $\theta 1$ with respect to the insertion axis Ax, but the present disclosure is not limited thereto. For example, the second guide grooves 113, 113A, and 113B may each be formed to extend inclinedly at the first angle $\theta 1$ with respect to the insertion axis Ax.

An endoscope according to the present disclosure has an effect of enabling reduction of wobbling of a treatment tool that has protruded from a distal end side of an insertion unit of the endoscope.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An endoscope comprising:
an insertion unit configured to be inserted into a subject, the insertion unit being configured to allow a treatment tool to protrude from a distal end thereof, the insertion unit including:
a rigid member having a treatment tool insertion hole where the treatment tool is inserted, the treatment tool insertion hole including:
an inclined insertion hole inclined with respect to an insertion axis that extends along an extending direction of the insertion unit, the inclined insertion hole extending from a distal end of the treatment tool insertion hole to a proximal end insertion hole; and
the proximal end insertion hole communicates with the inclined insertion hole, the proximal end insertion hole extending from the inclined insertion hole to a proximal end side of the treatment tool insertion hole;
a raising base turnably attached to the rigid member on a distal end side of the treatment tool insertion hole, the raising base being configured to adjust, by turning, a protruding direction of the treatment tool extending distally from the treatment tool insertion hole;
a first guide groove formed on an outer surface of the raising base, the first guide groove being configured to hold the treatment tool; and
a second guide groove formed on at least a part of an inner surface of the treatment tool insertion hole, the second guide groove including an opening having a width smaller than a diameter of the treatment tool insertion hole, the second guide groove extending over a boundary between the inclined insertion hole and the proximal end insertion hole,
wherein the first guide groove and the second guide groove are configured such that the treatment tool contacts both of the first guide groove and the second guide groove throughout an entire range of motion of the raising base, when the raising base is in a lowered state, the treatment tool comes into contact with:
the first guide groove of the raising base; and
only a proximal portion of the second guide groove; and when the raising base is in a raised state, the treatment tool comes into contact with:
the first guide groove of the raising base; and
only a distal portion of the second guide groove.

2. The endoscope according to claim 1, wherein the second guide groove has an arc-shaped cross section.

3. The endoscope according to claim 1, wherein the second guide groove is formed over the entire length of an inner surface of the inclined insertion hole.

4. The endoscope according to claim 1, wherein
the inclined insertion hole is inclined at a first angle with respect to the insertion axis, and
the second guide groove extends inclinedly at a second angle larger than the first angle, with respect to the insertion axis.

5. The endoscope according to claim 4, wherein an angle between an extension direction of the first guide groove and the insertion axis is smaller than the first angle.

6. The endoscope according to claim 1, wherein the second guide groove extends from an inner surface of the proximal end insertion hole to an inner surface of the inclined insertion hole.

7. The endoscope according to claim 1, wherein the rigid member includes:
a rigid member body that is made of resin; and
a connection member that is fixed to a proximal end of the rigid member body, is connected to a tube where the treatment tool is inserted, and is made of metal, and
the treatment tool insertion hole extends through both the rigid member body and the connection member and communicates with the tube connected to the connection member.

8. The endoscope according to claim 1, wherein the insertion unit further includes an ultrasound probe that is attached to a distal end of the rigid member and that transmits and receives ultrasound.

9. The endoscope according to claim 8, wherein the ultrasound probe is a convex ultrasound probe, and the treatment tool interposed between the first guide groove and the second guide groove is prevented from being displaced from a scanned surface of the ultrasound probe.

10. The endoscope according to claim 1, wherein when the raising base is in a lowered state, the treatment tool comes into contact with only the proximal portion of the second guide groove near the boundary between the inclined insertion hole and the proximal end insertion hole.

11. The endoscope according to claim 1, wherein the second guide groove extends distally to a distal opening of the treatment tool insertion hole.

12. An insertion unit for use with an endoscope, the insertion unit configured to be inserted into a subject and configured to allow a treatment tool to protrude from a distal end thereof, the insertion unit comprising:

a rigid member having a treatment tool insertion hole where the treatment tool is inserted, the treatment tool insertion hole including:
an inclined insertion hole inclined with respect to an insertion axis that extends along an extending direction of the insertion unit, the inclined insertion hole extending from a distal end of the treatment tool insertion hole to a proximal end insertion hole; and
the proximal end insertion hole communicates with the inclined insertion hole, the proximal end insertion hole extending from the inclined insertion hole to a proximal end side of the treatment tool insertion hole;

a raising base turnably attached to the rigid member on a distal end side of the treatment tool insertion hole, the raising base being configured to adjust, by turning, a protruding direction of the treatment tool extending distally from the treatment tool insertion hole;

a first guide groove formed on an outer surface of the raising base, the first guide groove being configured to hold the treatment tool; and a second guide groove formed on at least a part of an inner surface of the treatment tool insertion hole, the second guide groove including an opening having a width smaller than a diameter of the treatment tool insertion hole, the second guide groove extending over a boundary between the inclined insertion hole and the proximal end insertion hole, wherein the first guide groove and the second guide groove are configured such that the treatment tool contacts both of the first guide groove and the second guide groove throughout an entire range of motion of the raising base, when the raising base is in a lowered state, the treatment tool comes into contact with:
the first guide groove of the raising base; and
only a proximal portion of the second guide groove; and when the raising base is in a raised state, the treatment tool comes into contact with:
the first guide groove of the raising base; and
only a distal portion of the second guide groove.

13. The insertion unit according to claim 12, wherein
the inclined insertion hole is inclined at a first angle with respect to the insertion axis, and
the second guide groove extends inclinedly at a second angle larger than the first angle, with respect to the insertion axis.

14. The insertion unit according to claim 13, wherein an angle between an extension direction of the first guide groove and the insertion axis is smaller than the first angle.

15. The insertion unit according to claim 12, wherein when the raising base is in a lowered state, the treatment tool comes into contact with only the proximal portion of the second guide groove near the boundary between the inclined insertion hole and the proximal end insertion hole.

16. The insertion unit according to claim 12, wherein the second guide groove extends distally to a distal opening of the treatment tool insertion hole.

\* \* \* \* \*